United States Patent [19]
Kleiner et al.

[11] Patent Number: 5,891,226
[45] Date of Patent: Apr. 6, 1999

[54] SALTS OF PHOSPHONOUS ACIDS AND USE THEREOF AS FLAME RETARDANTS IN PLASTICS

[75] Inventors: Hans-Jerg Kleiner, Kronberg; Winfried Budzinsky; Günther Kirsch, both of Bad Soden, all of Germany

[73] Assignee: Ticona GmbH, Germany

[21] Appl. No.: 810,552

[22] Filed: Mar. 3, 1997

[30] Foreign Application Priority Data

Mar. 4, 1996 [DE] Germany .................. 196 08 006.1

[51] Int. Cl.$^6$ ........................... C09D 5/18; C08K 5/53
[52] U.S. Cl. ......................... 106/18.18; 106/18.15; 106/18.19; 252/601; 252/609; 428/920; 428/921; 524/115; 524/133; 524/147; 562/8
[58] Field of Search ............... 106/18.18, 18.15, 106/18.19; 252/601, 609; 524/115, 133, 147; 562/8; 427/384; 428/920, 921

[56] References Cited

U.S. PATENT DOCUMENTS

| | | | |
|---|---|---|---|
| 3,594,347 | 7/1971 | Lazarus et al. | 524/135 |
| 3,786,114 | 1/1974 | Jaquiss et al. | 524/138 |
| 3,809,676 | 5/1974 | Liberti | 524/135 |
| 3,855,134 | 12/1974 | Green et al. | 106/18.18 |
| 4,263,230 | 4/1981 | Uhing | 558/156 |
| 4,308,197 | 12/1981 | Byrd et al. | 428/272 |
| 4,328,132 | 5/1982 | Moberly | 106/18.18 |
| 4,377,537 | 3/1983 | Block et al. | 558/122 |
| 4,694,094 | 9/1987 | Juge et al. | 558/76 |
| 4,952,740 | 8/1990 | Juge et al. | 558/83 |
| 5,053,148 | 10/1991 | Von Bonin | 106/18.18 |
| 5,128,495 | 7/1992 | Scheffel et al. | 558/134 |
| 5,298,541 | 3/1994 | Bohshar et al. | 524/126 |
| 5,428,086 | 6/1995 | Minnick et al. | 524/126 |
| 5,498,745 | 3/1996 | Kleiner | 558/118 |

FOREIGN PATENT DOCUMENTS

| | | |
|---|---|---|
| 0 031 054 | 7/1981 | European Pat. Off. |
| 0 038 778 | 10/1981 | European Pat. Off. |
| 0 453 871 | 10/1991 | European Pat. Off. |
| 0 466 137 | 1/1992 | European Pat. Off. |
| 3 616 168 | 11/1987 | Germany |
| 58-150502 | 9/1983 | Japan |

OTHER PUBLICATIONS

Soviet Inventions Illustrated; Section Ch, Week 8021; Jul. 2, 1980; Derwent Publications Ltd., London, GB; Magdeeva R.K.: "Alkyl–Phosphonic Acid Preparation".

Chemical Abstract No. 112:78592 which is an abstract for an article by Devedjiev et al entitled "Effectiveness . . . Flame . . . Foams" (1989) [No Month].

Chemical Abstract Registry No. 81323–91–3 Phosphinic acid, methyl–, aluminum salt (Aluminum tris (methylphosphonite) (Sep. 1983).

WPIDS Abstract No. 85–313239 which is an abstract of Japanese Patent Specification No. 60–217256 (Oct. 1985).

WPIDS Abstract No. 88–001563 which is an abstract of Japanese Patent Specification No. 63–008453 (Nov. 1988).

WPIDS Abstract No. 91–353743 which is an abstract of PCT International Patent Application Specification No. 91/17209 (Nov. 1991).

WPIDS Abstract No. 93–216996 which is an abstract of Japanese Patent Specification No. 05–140421 (Jun. 1993).

WPIDS Abstract No. 94–062145 which is an abstract of Japanese Patent Specification No. 06–016914 (Jan. 1994).

WPIDS Abstract No. 97–214054 which is an abstract of German Patent Specification No. 19604195 (Apr. 1997).

*Primary Examiner*—Anthony Green
*Attorney, Agent, or Firm*—Connolly & Hutz

[57] ABSTRACT

Salts of phosphonous acids are useful as flame retardants in plastics. Preferred salts are calcium or aluminum salts of phenylphosphonous acid and of methanephosphonous acid. Plastic molding materials rendered flame-retardant in this way are useful for manufacturing molded parts, especially electrical components, mechanical components, plugs, mounts, housings, coverings, sheathings and overcoatings.

16 Claims, No Drawings

SALTS OF PHOSPHONOUS ACIDS AND USE THEREOF AS FLAME RETARDANTS IN PLASTICS

This invention relates to salts of phosphonous acids, processes for their preparation and their use as flame retardants in plastics.

BACKGROUND OF THE INVENTION

Polymers frequently become flame-resistive on addition of phosphorus or halogen compounds or mixtures thereof. Some polymers are processed at high temperatures, for example at 250° C. or higher. For this reason, many known flame retardants are unsuitable for such applications, since they are too volatile or insufficiently heat-resistant.

It is an object of the present invention to provide flame retardants which do not have the disadvantages of existing flame retardants. For example, the flame retardants shall be essentially non-volatile at elevated temperatures (e.g. at 250° C. or higher), simple and inexpensive to prepare, exhibit good flame retardancy and have high temperature resistance at the elevated temperatures discussed above.

SUMMARY OF THE INVENTION

It has now been found that, surprisingly, salts of phosphonous acids are useful as flame retardants in plastics. The invention accordingly provides salts of phosphonous acids and processes for preparing them. The invention further provides plastics or plastic molding materials comprising at least one salt of a phosphonous acid. The invention further provides for the use of a salt of a phosphonous acid as a flame retardant in plastics.

Phosphonous acid is the designation for organically substituted phosphonous acids of the formula $$RHP(O)(OH),$$

where

R is the organic radical; preferably, R is defined as:
a straight-chain or branched $C_1$–$C_{12}$-alkyl radical, preferably
a branched or unbranched $C_1$–$C_8$-alkyl radical, especially $C_1$–$C_4$-alkyl, such as methyl, ethyl, propyl, isopropyl, n-butyl, s-butyl, t-butyl, pentyl, hexyl, heptyl, octyl, nonyl, decyl; or
an ether-substituted $C_1$–$C_{12}$-alkyl radical, such as alkoxyethyl, di-alkoxymethyl, phenoxymethyl; or
an arylalkyl radical such as benzyl; or
a cycloalkyl radical such as cyclohexyl; or
an unsubstituted or substituted aryl radical such as phenyl, pyridyl, naphthyl, halophenyl (chlorophenyl), methylphenyl, isopropylphenyl or hydroxynaphthyl.

Methanephosphonous acid, $CH_3HP(O)(OH)$, is a particularly preferred starting material for making salts useful in the present invention. Benezenephosphonous acid is another preferred embodiment of the starting material.

The salts of the aforementioned phosphonous acids (phosphonites) can be metal salts or nonmetal salts in which the acidic hydrogen has been replaced by a cation-forming species such as a metal or a nitrogen-containing organic radical (e.g. an ammonium-forming radical). Metal salts are normally preferred. The metal salts can contain a metal of the second or third main or sub group of the Periodic Table. Examples are alkali metals such as sodium and potassium; alkaline earth metals, such as magnesium, calcium, barium. Further examples are aluminum, zinc and zirconium. Preferred metal salts are calcium and aluminum salts. Nonmetal salts contain for example ammonium or alkylammonium salts. Optionally, mixtures of these salts can be used. Preferred salts of phosphonous acid are the calcium and aluminum salts, with the aluminum salts being particularly preferred.

The preferred salts can be represented by the formula $$RHP(O)(OM_{1/n}),$$

where R is one of the preferred radicals mentioned above, M is a cation-forming non-metallic group (such as a group that forms an ammonium cation) or a cation-forming metal, and n is the valence of M. In the case of metal salts, M is generally 1, 2, or 3.

The preferred metal salts can be prepared from the aforementioned phosphonous acids in aqueous solution by reaction with the corresponding metal carbonates, metal hydroxides or metal oxides. For this, in general, the phosphonous acid is dissolved in water and admixed, advantageously by stirring, with the corresponding metal hydroxide, metal carbonate or metal oxide in stoichiometric amounts. The reaction mixture is then generally heated, preferably to a temperature range from 30° to 150° C., especially 70° to 110° C., and stirred for several hours. The reaction times range from a few hours (at least 5 hours) to several days (1 to 7 days). After the reaction has taken place, the reaction mixture is worked up by customary methods (cooling, filtration with suction, washing, drying, etc.). As is known in the art, non-metal salts are prepared in an analogous manner.

The starting compounds are known in the art and are commercially available or they can be prepared by known commonly used processes.

Plastics are generally thermoplastics such as polyesters, polyamides, polyolefins. Preferred polyesters are polyethylene terephthalate (PET) and polybutylene terephthalate (PBT). Preferred polyamides are nylon 66 and nylon 46.

Polyamides and polyesters which can be used for the purposes of this invention are described for example in "Ullmann's Encyclopedia of Industrial Chemistry, ed. Barbara Elvers, Vol. A21,-Polyamide' (p. 179–205) and Polyesters' (p. 227–251), VCH Publishers, Weinheim-Basel-Cambridge-New York 1992", incorporated herein by reference.

The amount of phosphonite to be added to the plastics can vary within wide limits. In general, 5 to 30% by weight, preferably 10 to 20% by weight, are used, based on the polymer. The most suitable amount depends on the nature of the polymer and the nature of the salt used and can be readily ascertained by experimentation.

Phosphonites can be used in various physical forms, depending on the nature of the polymer used and the desired properties. For instance, they can be ground to a finely divided form, for example for achieving a better dispersion in the polymer. As indicated previously, mixtures of various phosphonites are also useful.

The phosphonites used are generally sufficiently thermally stable, do not decompose the polymers during processing (e.g. at temperatures of at least 250° C.) and do not adversely affect the process of producing the plastic molding material. The fact that the phosphonites are thermally stable is surprising, since it is known that their parent phosphonous acids decompose at about 130° to 200° C. The phosphonites are generally not volatile under production and processing conditions for polymers.

The phosphonite can be incorporated into the polymer by a variety of known techniques. In the context of this invention, "incorporating" the phosphite is thus not limited to any specific physical combination procedure or any particular phase of the polymer (molten, solid, prepolymeric, etc.), but chemical incorporation (where, for example, a salt is linked into the polymer molecule) is not required; physical combinations of the salt and the polymer provide the desired benefits of this invention.

In one preferred physical combining procedure, the polymer and the salt are mixed together; the polymer portion of the resulting mixture is melted in a compounder (a twin-screw extruder, for example); and the phosphonite is homogenized in the polymer melt. The melt can be extruded, cooled and granulated. The salt can also be metered directly into the compounder.

It is ordinarily especially convenient to incorporate the salt in a form which is as compatible as possible with the polymer or plastic to be rendered flame retardant. Such especially convenient forms include particulate plastic masses (particularly plastic granules) containing a minor amount of the salt or particulate (e.g. granular) masterbatches containing much higher percentages of salt (e.g. 30 to 80 or 90% by weight, based on the weight of the masterbatch). In these forms, the phosphonite can be mixed into a plastic which lacks flame-retardant properties. Moreover, finished granular polymer containing the desired amount of flame-retardant salt (e.g. 5 to 30% by weight of the polymer) can serve as a suitable molding material without further modification. For example, a mass of such granular polymer can be processed directly on an injection molding machine.

Alternatively, a mixture can first be melted in an extruder, granulated, and processed after drying.

Incorporation of the phosphonites can also be accomplished in condensation-polymerized plastics, e.g. in polyesters, during an early stage in the manufacture of the product, e.g. during the polycondensation. In this or any of the other incorporation procedures, the product which results is a flame-retardant plastic or polymer, typically in the form of a moldable material or in the form of a material which has already been shaped.

The flame-retardant plastic or polymer can contain, in addition to a flame-retardant phosphonite or mixture of phosphonites, a variety of conventional components which provide or alter the color, the stability, the physical properties of the plastic, and the like. The use of these known ingredients is well known and need not be described in detail. Thus, the plastics can also have added to them fillers and reinforcing materials such as glass fibers, glass balls or minerals such as chalk, UV stabilizers, lubricants, colorants, pigments, nucleating agents, antistatic agents, or various combinations of these components.

The plastics, such as polyamides and polyesters, rendered flame-retardant using a phosphonite are typically in the form of a molding material and thus are useful for manufacturing shaped articles, which broadly includes films, coatings, filaments and fibers as well as more massive three-dimensional objects. Typical molding procedures useful in this invention include injection, extrusion or press molding.

Phosphonite-comprising plastics, especially polyesters and polyamides, are notable for a high tracking current resistance (high CTI). Accordingly, shaped objects made in accordance with this invention can include a wide variety of electrical, electronic, and mechanical (including electromechanical) components. Examples of such components include:

Coil formers, transformers, relays, switches, plug connectors, motors and motor parts (rotors, bearing plates, etc.), molded interconnection devices (MIDs), bases (e.g. SIMM bases), mechanical components in electrical and household appliances, for example gearwheels, levers, camshafts, spacers, hinges, sliding bearings, housings, coverings, sheathings and coatings of electrical devices and appliances, for example capacitor housings, relay housings, capacitor covers, cable sheathings.

Further examples of shaped articles include plugs, mounts, housings, coverings, sheathings, overcoatings. Coatings can be applied to a variety of known substrates.

Thus, phosphonites can also be included in coatings such as fire protection coatings, especially fire protection coatings for plastics such as polyoxymethylene, polyester or polyamide.

The invention accordingly also provides for the use of phosphonites as a constituent of coatings, especially of fire protection coatings.

EXAMPLES

Preparation of salts of phosphonous acid

1. Preparation of the calcium salt of benzenephosphonous acid 426 g (3.0 mol) of benzenephosphonous acid are dissolved in 852 g of water by heating to 60° C.

111 g (1.5 mol) of calcium hydroxide are added a little at a time with vigorous stirring over 40 minutes. This is followed by stirring at 90° C for 8 hours, cooling, filtration with suction and washing with water. Drying the filter cake in a vacuum drying cabinet at 130° C. leaves 432 g.

Yield: about 90% of theory.

Melting point: >360° C.

2. Preparation of the aluminum salt of benzenephosphonous acid 568 g (4.0 mol) of benzenephosphonous acid are dissolved in 1140 g of water by heating to 60° C.

104 g (1.33 mol) of aluminum hydroxide are added with vigorous stirring while heating to 90° C. In total the mixture is stirred at 85°–90° C. for 68 hours, then cooled, filtered with suction and washed with water. Drying at 130° C. in a vacuum drying cabinet to constant weight leaves 561 g of white powder.

Yield: 93.5% of theory

Melting point: >320° C.

3. Preparation of the aluminum salt of methanephosphonous acid 528 g (6.6 mol) of methanephosphonous acid are dissolved in 700 g of water and 171.6 g (2.2 mol) of aluminum hydroxide are added with vigorous stirring while heating to 85° C. In total the mixture is stirred at 80°–90° C. for 48 hours, then cooled, filtered with suction and washed with water. Drying leaves 485 g of a white powder.

Yield: about 84% of theory.

Melting point: >315° C.

3.1 Production and testing of flame-retardant polyester

The application of the aluminum salt of methanephosphonous acid in polybutylene terephthalate (PBT) was tested. To this end, the aluminum salt of methanephosphonous acid according to Example 3 was mixed with the polymer and incorporated on a commercially available twin-screw compounder. In the case of glass fiber reinforced products, 30% by weight of glass fibers customary for polyester were metered into the melt. The melt temperature during the compounding was about 250° C. The test specimens were produced on an injection molding machine to ISO 7792-2. The UL 94 (Underwriters Laboratories) materials classification was determined on test specimens 0.8 mm in thickness.

In a first trial, the molding material comprises 30% by weight, based on the weight of PBT, of the aluminum salt of methanephosphonous acid according to Example 3. The materials classification of V-0 was achieved. In a second trial using a 20% by weight concentration of the aluminum salt, based on the weight of PBT, the materials classification achieved was again V-0.

What is claimed is:

1. A method for improving the flame-retardancy of a plastic which comprises incorporating into a plastic wherein the plastic is a polyester, polyamide, polyolefin or a mixture thereof a flameproofing amount of at least one phosphonite salt of the formula $$RHP(O)(OM_{1/n}),$$

where

R is a straight-chain or branched $C_1$–$C_{12}$-alkyl radical, or
an ether-substituted $C_1$–$C_{12}$-alkyl radical, or
an arylalkyl radical, or
a cycloalkyl radical, or
an unsubstituted or substituted aryl radical;

M is calcium or aluminum, and n is the valence of M.

2. The method as claimed in claim 1, wherein R is phenyl or methyl.

3. The method as claimed in claim 1, wherein, after incorporation, the resulting plastic contains 5 to 30% by weight of phosphonite salt.

4. The method as claimed in claim 3, wherein said resulting plastic contains from 10 to 20% by weight of phosphonite salt.

5. A composition comprising a plastic wherein said plastic is a polyester, polyamide, polyolefin or a mixture thereof and contains a flameproofing amount of at least one phosphonite salt of the formula $$RHP(O)(OM_{1/n}),$$

where

R is a straight-chain or branched $C_1$–$C_{12}$-alkyl radical, or
an ether-substituted $C_1$–$C_{12}$-alkyl radical, or
an arylalkyl radical, or
a cycloalkyl radical or
an unsubstituted or substituted aryl radical;

M is calcium or aluminum, and n is the valence of M.

6. The composition as claimed in claim 5, wherein R is a substituted or unsubstituted $C_1$–$C_{12}$-alkyl or aryl radical.

7. The composition as claimed in claim 5, wherein R is phenyl or methyl.

8. The composition as claimed in claim 5, wherein the plastic contains a condensation polymer.

9. The composition as claimed in claim 5, wherein phosphonite salt is present in an amount from 5 to 30% by weight of said composition.

10. The composition as claimed in claim 9, wherein phosphonite salt is present in an amount from 10 to 20% of said composition.

11. The composition as claimed in claim 5, wherein said composition is a particulate masterbatch containing up to 90% by weight of phosphonite salt, based on the weight of the masterbatch.

12. A molded part containing a plastic wherein the plastic is a polyester, polyamide, polyolefin or a mixture thereof and contains a flameproofing amount of at least one salt of a phosphonite salt of the formula $$RHP(O)(OM_{1/n}),$$

where

R is a straight-chain or branched $C_1$–$C_{12}$-alkyl radical, or
an ether-substituted $C_1$–$C_{12}$-alkyl radical, or
an arylalkyl radical, or
a cycloalkyl radical, or
an unsubstituted or substituted aryl radical;

M is calcium or aluminum, and n is the valence of M.

13. The molded part as claimed in claim 12, wherein said molded part is an electrical or electronic component.

14. The molded part as claimed in claim 12, wherein said molded part is a mechanical component.

15. The molded part as claimed in claim 12, where said molded part is a plug, a mount, a housing, a covering, a sheathing, or an overcoating.

16. A method for improving the fire protection of an object, which comprises coating an object with a coating containing a phosphonite salt of the formula $$RHP(O)(OM_{1/n}),$$

where

R is a straight-chain or branched $C_1$–$C_{12}$-alkyl radical, or
an ether-substituted $C_1$–$C_{12}$-alkyl radical, or
an arylalkyl radical, or
a cycloalkyl radical, or
an unsubstituted or substituted aryl radical;

M is calcium or aluminum; and n is the valence of M.

* * * * *